(12) United States Patent
Koike et al.

(10) Patent No.: US 6,448,292 B2
(45) Date of Patent: Sep. 10, 2002

(54) OIL COMPOSITION

(75) Inventors: Shin Koike; Naoki Hosoya; Takeshi Yasumasu, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/809,192

(22) Filed: Mar. 16, 2001

(30) Foreign Application Priority Data

Mar. 21, 2000 (JP) .......................................... 2000-078110

(51) Int. Cl.⁷ ............................................... A61K 31/20
(52) U.S. Cl. ........................................ 514/558; 514/560
(58) Field of Search ................................ 514/558, 560

(56) References Cited

U.S. PATENT DOCUMENTS

| | | | |
|---|---|---|---|
| 5,160,759 A | * 11/1992 | Nomura et al. | 426/602 |
| 6,337,414 B1 | 1/2002 | Sugiura et al. | 554/174 |

FOREIGN PATENT DOCUMENTS

| | | |
|---|---|---|
| JP | 63-104917 | 5/1988 |
| JP | 1-174342 | 7/1989 |
| JP | 4-300825 | 10/1992 |
| JP | 4-300826 | 10/1992 |
| JP | 4-300828 | 10/1992 |
| JP | 8-60181 | 3/1996 |
| JP | 8-214892 | 8/1996 |
| JP | 10-57086 | 3/1998 |
| JP | 10-265795 | 10/1998 |
| JP | 10265795 | * 10/1998 |

OTHER PUBLICATIONS

Yukihisa Tanaka et al., JAOCS, vol. 69, No. 12, pp. 1210–1214, "Concentration of Docosahexaenoic Acid in Glyceride by Hydrolysis of Fish Oil with Candida Cylindracea Lipase," Dec. 1992.

* cited by examiner

Primary Examiner—Kevin E. Weddington
(74) Attorney, Agent, or Firm—Oblon, Spivak, McClelland, Maier & Neustadt, P.C.

(57) ABSTRACT

Disclosed herein is an oil composition containing a diglyceride, in which at least 55% by weight of the constitutive acyl groups are unsaturated acyl groups, and 15 to 100% by weight thereof are ω3 type unsaturated acyl groups having at least 20 carbon atoms, in an amount of not less than 10% by weight, but less than 40% by weight, and a triglyceride, in which at least 70% by weight of the constitutive acyl groups are unsaturated acyl groups, and 5 to 80% by weight thereof are a linoleyl group, in an amount of 40.1 to 89.8% by weight. The composition effectively develops the physiological functions derived from ω3 type unsaturated fatty acids, such as antiarteriosclerotic effect, and is excellent in oxidation stability, flavor and the like. Foods and medicines containing such an oil composition are provided.

11 Claims, No Drawings

OIL COMPOSITION

BACKGROUND OF THE INVENTION

1. Field of the Invention

The present invention relates to an oil or fat (hereafter referred to as "oil" merely) composition which effectively develops physiological functions derived from ω3 type unsaturated fatty acids, such as antiarteriosclerotic effect, and is excellent in oxidation stability, flavor and the like, and foods and medicines comprising such an oil composition.

2. Description of the Background Art

In recent years, it has been clarified that diglycerides have an obesity-preventing effect, an effect to prevent an increase in weight, etc. (Japanese Patent Application Laid-Open Nos. 300828/1992, 300826/1992 and 300825/1992, etc.), and it is attempted to incorporate these into various kinds of foods.

On the other hand, it has been known that ω3 type unsaturated fatty acids such as docosahexaenoic acid (DHA) and eicosapentaenoic acid (EPA) are mainly contained in the form of triglyceride in fish oil and the like in plenty and have effective physiological activities such as antiarteriosclerotic effect, antitumor activity, immune activation, antiallergic activity, improvement in brain function and improvement in visual function.

As oils highly containing such diglycerides and ω3 type unsaturated fatty acids, there have been known, for example, a natural oil that DHA among constitutive fatty acids of the oil is contained in a proportion of at least 60%, and the total content of diglycerides and monoglycerides is at least 80% of the oil (Japanese Patent Application Laid-Open No. 60181/1996), and the like. In addition, there has been known a high unsaturated fatty acid-containing oil composition having a glyceride composition that the total amount of monoglycerides and diglycerides is greater than the amount of triglycerides, and enhanced in hydration property (Japanese Patent Application Laid-Open No. 265795/1998).

However, the ω3 type unsaturated fatty acids are very poor in oxidation stability. When a ω3 type unsaturated fatty acid is oxidized, the oxidized unsaturated fatty acid involves a problem that not only its physiological activity functions are lost, but also the a living body is adversely affected when such an unsaturated fatty acid is taken. In addition, a ω3 type unsaturated fatty acid-containing oil has an unpleasant flavor derived from its raw oil, and so a problem is offered when it is used in food in particular. Further, ω3 type unsaturated fatty acids involve a problem that when they are converted into their corresponding diglycerides, the diglycerides do not become liquid at the temperature of the living body, so that the physiological activities of the ω3 type unsaturated fatty acids are hard to be developed.

There is a demand for solution of a conflicting problem that when a ω3 type unsaturated acyl content is lowered in order to avoid these problems, the development of the physiological activity functions, which is an object of incorporation, is deteriorated.

SUMMARY OF THE INVENTION

It is therefore an object of the present invention to provide an oil composition which is hard to be oxidized, is excellent in flavor and liquid at the temperature of a living body and has high physiological activities of ω3 type unsaturated fatty acids, and foods and medicine comprising such an oil composition.

The present inventors have attracted attention to the compositions of acyl groups constituting a diglyceride and a triglyceride and found that when ω3 type unsaturated acyl groups as acyl groups constituting a diglyceride and a linoleyl group (cis,cis-9,12-octadecadienoyl group) as an acyl group constituting a triglyceride are contained in specified amounts in an oil composition comprising a diglyceride in a specified amount, the above object can be achieved.

According to the present invention, there is thus provided an oil composition comprising a diglyceride, in which at least 55% by weight (hereafter indicated merely by "%") of the constitutive acyl groups are unsaturated acyl groups, and 15 to 100% thereof are ω3 type unsaturated acyl groups having at least 20 carbon atoms, in an amount of not less than 10%, but less than 40%, and a triglyceride, in which at least 70% of the constitutive acyl groups are unsaturated acyl groups, and 5 to 80% thereof are a linoleyl group, in an amount of 40.1 to 89.8%.

According to the present invention, there is also provided a food comprising such an oil composition.

According to the present invention, there is further provided a medicine comprising such an oil composition.

DETAILED DESCRIPTION OF THE PREFERRED EMBODIMENTS

In the present invention, the acyl groups constituting a diglyceride include ω3 unsaturated acyl groups having at least 20 carbon atoms, preferably 20 to 24 carbon atoms in a proportion of 15 to 100%, preferably 20 to 90%, particularly preferably 40 to 70% based on all the acyl groups in the diglyceride. In order to effectively achieve the physiologically active effect of ω3 type unsaturated fatty acids, it is necessary to contain ω3 unsaturated acyl groups having at least 20 carbon atoms in an amount of at least 15%. The term "ω3 type unsaturated fatty acid" as used herein means an acyl group that a first unsaturated bond is located on the third carbon atom from a ω position when the positions of unsaturated bonds are specified from the ω position, and that has at least 2 unsaturated bonds. As the ω3 type unsaturated acyl groups having at least 20 carbon atoms, are particularly preferred eicosapentaenoyl and docosahexaenoyl groups.

In the present invention, the number of carbon atoms in remaining acyl groups constituting the diglyceride is preferably 8 to 24, particularly 16 to 22. In order to maintain the oil composition according to the present invention in a liquid state at the temperature of a living body, the unsaturated acyl groups must be contained in a proportion of at least 55%, preferably at least 70%, particularly preferably at least 80% based on all the acyl groups in the diglyceride.

The unsaturated acyl groups are preferably contained in a proportion of at most 98% from the viewpoints of production cost and effect.

The diglyceride can be obtained by an optional process such as transesterification of any of various oils such as fish oil and rapeseed oil containing ω3 type unsaturated acyl groups, monoenoic acyl groups with glycerol and the like or esterification of a fatty acid derived from such an oil with glycerol. The reaction method thereof may be either a chemical reaction method making use of an alkali catalyst or the like or a biochemical reaction method making use of an enzyme such as lipase. The content of such a diglyceride in the oil composition according to the present invention must be not lower than 10%, but lower than 40%, and is particularly preferably 15 to 35%. When the content is not lower than 10%, but lower than 40%, the development of physiological activities derived from the (93 type unsaturated fatty acids is easily consistent with oxidation stability in cooperation with a linoleyl group in the triglyceride.

In the present invention, the acyl groups constituting a triglyceride include a linoleyl group in a proportion of 5 to 80%, preferably 7 to 55%, more preferably 7 to 45%, particularly preferably 10 to 30% based on all the acyl groups in the triglyceride. In order to maintain the oil composition according to the present invention in a liquid state at the temperature of a living body and to avoid side effect by ω3 type unsaturated fatty acids, the linoleyl group must be contained in a proportion of at least 5% based on all the acyl groups in the triglyceride. The linoleyl group may be preferably contained in a proportion of at most 80% from the viewpoints of the physiologically active effect of the ω3 type unsaturated fatty acids and oxidation stability.

In the present invention, the number of carbon atoms in remaining acyl groups constituting the triglyceride is preferably 8 to 24, particularly 16 to 22. In order to maintain the oil composition according to the present invention in a liquid state at the temperature of a living body, the unsaturated acyl groups must be contained in a proportion of at least 70%, preferably at least 75%, more preferably at least 80, particularly preferably at least 90% based on all the acyl groups in the triglyceride. The unsaturated acyl groups are preferably contained in a proportion of at most 98% from the viewpoints of production cost and effect. The ω3 type unsaturated acyl groups are preferably contained in a proportion of at most 30%, more preferably at least 20% based on all the acyl groups in the triglyceride from the viewpoint of oxidation stability. The ω6 type unsaturated acyl groups such as a γ-linolenyl group (all cis-6,9,12-octadecatrienoyl group) and an arachidonyl group (all cis-5,8,11,14-eicosatetraenoyl group) are preferably contained in a proportion of at most 5%, more preferably at least 2%, particularly preferably 0% based on all the acyl groups in the triglyceride from the viewpoint of oxidation stability. The triglyceride can be obtained from a vegetable oil such as soybean oil, rapeseed oil, palm oil, rice oil or corn oil, an animal oil such as beef tallow or fish oil, or a hardened oil, fractionated oil or random transesterified oil thereof. The content of the triglyceride in the oil composition according to the present invention is preferably 40.1 to 89.8%, particularly 50 to 80% from the viewpoint of masking of flavor derived from the raw oil.

The triglyceride preferably contains monoenoic acyl groups in a proportion of 10 to 85%, more preferably 15 to 70%, particularly preferably 25 to 60% based on all the acyl groups. The monoenoic acyl group is an acyl group having a carbon-carbon double bond and 8 to 24 carbon atoms, preferably 16 to 22 carbon atoms. As examples of the monoenoic acyl groups, are particularly preferred hexadecamonoenoyl, octadecamonoenoyl, eicosamonoenoyl and docosamonoenoyl groups.

The content of a monoglyceride in the oil composition according to the present invention is preferably 0.1 to 10%, more preferably 0.1 to 5%, particularly preferably 0.1 to 2%, still more preferably 0.1 to 1.5% from the viewpoint of improvement in the flavor of the oil composition. The content of free fatty acids is preferably at most 2%, more preferably at most 1%, particularly preferably at most 0.5% from the viewpoint of improvement in the flavor of the oil composition.

In the present invention, a glyceride polymer may preferably be contained in order to improve the oxidation stability. The glyceride polymer is obtained by intermolecular polymerization of a glyceride such as a triglyceride, diglyceride or monoglyceride (for example, "Kagaku to Seibutu (Chemistry and Organism), Vol. 21, page 179, 1983), and no particular limitation is imposed on the polymerization degree of the glyceride, the positions of fatty acid esters, the kinds of acyl groups constituting the fatty acid esters, etc. The content of the glyceride polymer in the oil composition is preferably 0.1 to 10%, more preferably 0.1 to 5%, particularly preferably 0.2 to 2% from the viewpoints of improvement in oxidation stability and flavor of the oil composition. The amount of such a glyceride polymer can be controlled by suitably controlling reaction temperature conditions and the like upon synthesis of the glyceride polymer. The glyceride polymer can be determined by an HPLC process in which a gel permeation chromatographic column is connected.

The oil composition according to the present invention can be prepared by mixing the above-described components and suitably subjecting the resulting mixture to heating, stirring and/or the like. Alternatively, the oil composition can be obtained by transesterification of an oil containing ω3 type unsaturated acyl groups, a linoleyl group, monoenoic acyl groups and the like, such as fish oil or rapeseed oil, with glycerol, or the like. It may also be prepared by fractionating triglycerides, diglycerides, monoglycerides, glyceride polymers, free fatty acids and the like from the resulting transesterification product, and then suitably mixing these fractionation products with one another, and optionally mixing an ordinary edible oil such as soybean oil, rapeseed oil or perilla oil therewith. A preparation process by transesterification of an oil containing ω3 type unsaturated acyl groups, a linoleyl group, monoenoic acyl groups and the like with an ordinary edible oil and glycerol, and a process, in which an ordinary edible oil is mixed with a transesterification product of an oil containing ω3 type unsaturated acyl groups, a linoleyl group, monoenoic acyl groups and the like with glycerol are more preferred.

An antioxidant may be added to the oil composition according to the present invention. Any antioxidant may be added so far as it is commonly used in foods and medicines. However, one of catechin, tocopherol, vitamin C fatty acid esters and natural antioxidant components, or a combination of two or more components thereof is preferred, with catechin being particularly preferred. Examples of the vitamin C fatty acid esters include the palmitate and stearate, and examples of the natural antioxidant components include extracts from herbs such as rosemary, and leaves and roots of peach. The antioxidant is preferably added in a proportion of 0.01 to 5%, particularly 0.05 to 1% to the oil composition according to the present invention.

The oil composition thus obtained has excellent physiological activities such as effects of facilitating combustion of body fat, reducing blood sugar, consuming triglyceride in blood, reducing insulin in blood, improving liver function, reducing blood pressure, and reducing plasminogen activator inhibitor type 1 (PAI-1) in addition to antiarteriosclerotic effect, based on its cell membrane fluidity-improving effect and the like, is good in digestibility because it is liquid at the temperature of a living body, can be stored over a long period of time because it is excellent in oxidation stability, and moreover is excellent in flavor. In particular, since the ω3 type unsaturated acyl groups are present as acyl groups constituting a diglyceride, the oil composition acts at a lower concentration than the case where they are present as free fatty acids, and so it has good fast-acting property, and is good in flavor and safe. Since the oil composition according to the present invention has such excellent properties, it can be utilized for foods and medicines.

With respect to the foods, the oil composition may be used as oil-containing foods containing the oil composition as a part of food. Examples of such oil-containing foods include healthy foods that the specified functions are exhibited to promote health. Specific examples thereof include capsule preparations, tablet preparations, granule preparations, bakery foods such as bread and cookie, dressings such as French dressing, mayonnaises, creams, confectionery such as chocolates and potato chips, and drinks, in which such an oil composition is incorporated. Such oil-containing food can be produced by adding food materials commonly used according to the kind of the oil-containing food in addition to the oil composition in accordance with a method known per se in the art. It is preferred that the amount of the oil composition according to the present invention to be incorporated in food be generally 0.1 to 100%, particularly 1 to 80% though it varies according to the kind of the food. It may also be used as a food material of oils for fried foods such as tempura and fries, or oils for frizzled foods.

No particular limitation is imposed on the forms of the medicines, and examples thereof include oral preparations, such as solid preparations such as powder preparations, granule preparations, capsule preparations, pill preparations and tablet preparations; and liquid preparations such as aqueous preparations, suspension preparations and emulsion preparations. Such an oral preparation can be prepared by adding an excipient, a disintegrator, a binder, a lubricant, a surfactant, an alcohol, water, a water-soluble polymer, an edulcorant, a taste corrigent, an acid corrigent and/or the like commonly used according to the form of the oral preparation in addition to the oil composition in accordance with a method known per se in the art. Examples of medicines for oral administration include platelet aggregation inhibitors, brain function improvers and visual function improvers. It is preferred that the amount of the oil composition according to the present invention to be incorporated in the oral preparation be generally 0.1 to 100%, particularly 1 to 80% though it varies according to the application and form of the medicine. With respect to the dose of the oil composition as a medicament, it is preferably administered in a dose of 0.1 to 50 g per day. Meanwhile, the administration may be once per day, or may be divided into several times per day.

EXAMPLE 1

Rapeseed oil (product of Nisshin Oil Mills Ltd.; 100 parts by weight), a high DHA-containing oil ("DHA-45", product of MARUHA CORP.; 100 parts by weight) and glycerol (product of Wako Pure Chemical Industries, Ltd.; 8 parts by weight) were mixed with one another, and an alkali catalyst (sodium methoxide, $CH_3ONa$; 0.5 parts by weight) was mixed to the resultant mixture to conduct transesterification at 100° C. for 4 hours under reduced pressure (0.133 kPa). The reaction product thus obtained was fractionated by column chromatography on silica gel, and a triglyceride (64.9 parts by weight), a diglyceride (34.8 parts by weight), a monoglyceride (0.2 parts by weight) and a free fatty acid (0.1 parts by weight) were mixed with the resultant fractionation product to prepare Oil Composition 1.

EXAMPLE 2

Olive oil (product of Wako Pure Chemical Industries, Ltd.; 120 parts by weight), a high EPA-containing oil ("EPA28", product of NIPPON SUISAN, INC.; 80 parts by weight) and glycerol (8 parts by weight) were mixed with one another to conduct transesterification and fractionation of respective components in a similar manner to Example 1. A triglyceride (79.2 parts by weight), a diglyceride (22.4 parts by weight), a monoglyceride (0.1 parts by weight), a free fatty acid (0.1 parts by weight) and a glyceride polymer (0.2 parts by weight) were then mixed with the resultant fractionation product to prepare Oil Composition 2.

EXAMPLE 3

Purified fish oil (product of Kao Corporation; 200 parts by weight) and glycerol (8 parts by weight) were mixed with each other to conduct transesterification and fractionation of respective components in a similar manner to Example 1. A diglyceride (10 parts by weight), a monoglyceride (0.1 parts by weight), a glyceride polymer (0.2 parts by weight) and perilla oil (product of OHTA OIL MILL CO., LTD.; 89.7 parts by weight) were then mixed with the resultant fractionation product to prepare Oil Composition 3.

EXAMPLE 4

A high DHA-containing oil ("DHA-45", product of MARUHA CORP.; 100 parts by weight) and glycerol (6 parts by weight) were mixed with each other to conduct transesterification and fractionation of respective components in a similar manner to Example 1. A diglyceride (23.5 parts by weight), a monoglyceride (0.2 parts by weight), a free fatty acid (0.1 parts by weight), a glyceride polymer (0.1 parts by weight) and rapeseed oil (product of Nisshin Oil Mills, Ltd.; 76.1 parts by weight) were then mixed with the resultant fractionation product to prepare Oil Composition 4.

EXAMPLE 5

A high DHA-containing oil ("DD Oil Type 3G", product of NIPPON SUISAN, INC.; 100 parts by weight) and glycerol (6 parts by weight) were mixed with each other to conduct transesterification and fractionation of respective components in a similar manner to Example 1. A triglyceride (20.0 parts by weight), a diglyceride (16.9 parts by weight), a monoglyceride (1.1 parts by weight), a free fatty acid (0.1 parts by weight), a glyceride polymer (0.2 parts by weight) and soybean oil (product of Nisshin Oil Mills, Ltd.; 61.7 parts by weight) were then mixed with the resultant fractionation product to prepare Oil Composition 5.

EXAMPLE 6

A high DHA-containing oil ("DHA-45", product of MARUHA CORP.; 100 parts by weight), glycerol (4 parts by weight) and sodium methoxide (0.3 parts by weight) were mixed with one another to conduct transesterification at 100° C. for 4.5 hours under reduced pressure (0.133 kPa). The resultant reaction product was subjected to molecular distillation (210° C., 0.00266–0.00666 kPa) and then decolorized and deodorized. A composition obtained in this stage contained 44.5% of triglyceride, 53.8% of diglyceride, 0.6% of monoglyceride, 0.1% of free fatty acid and 1.0% of glyceride polymer. Fifty parts by weight of this composition and 50 parts by weight of rapeseed oil (product of Nisshin Oil Mills, Ltd.) were mixed with each other to prepare Oil Composition 6. The thus-obtained Oil Composition 6 contained 71.8% of triglyceride, 27.3% of diglyceride, 0.3% of monoglyceride, 0.1% of free fatty acid and 0.5% of glyceride polymer.

EXAMPLE 7

A high DHA-containing oil ("DHA-45", product of MARUHA CORP.; 100 parts by weight), soybean oil (product of Nisshin Oil Mills, Ltd.; 100 parts by weight), glycerol (0.5 parts by weight) and sodium methoxide (0.5 parts by weight) were mixed with one another to conduct transesterification at 100° C. for 4 hours under reduced pressure (0.133 kPa). The resultant reaction product was subjected to molecular distillation (210° C., 0.00266–0.00666 kPa) and then decolorized and deodorized to prepare Oil Composition 7. The thus-obtained Oil Composition 7 contained 78.2% of triglyceride, 20.1% of diglyceride, 0.3% of monoglyceride, 0.1% of free fatty acid and 1.3% of glyceride polymer.

COMPARATIVE EXAMPLES 1 AND 2

Soybean oil (product of Nisshin Oil Mills, Ltd.) and fish oil (product of Kao Corporation) were provided as Oil Composition 8 (Comparative Example 1) and Oil Composition 9 (Comparative Example 2).

COMPARATIVE EXAMPLE 3

The transesterification and fractionation product of Example 3 was used and mixed with a triglyceride (71.7 parts by weight), a diglyceride (27.8 parts by weight), a monoglyceride (0.1 parts by weight) and a free fatty acid (0.4 parts by weight) to prepare Oil Composition 10.

COMPARATIVE EXAMPLE 4

The transesterification and fractionation product of Example 3 was used and mixed with a triglyceride (36.4 parts by weight) and a diglyceride (63.6 parts by weight) to prepare Oil Composition 11.

Principal fatty acid compositions of diglyceride and triglyceride fractions derived from the respective oil compositions obtained in Examples 1 to 7 and Comparative Examples 3 and 4 are shown in Tables 1 and 2, respectively.

TABLE 1

Principal fatty acid composition in diglyceride

| | | Example | | | | | | | Comp. Ex. | |
|---|---|---|---|---|---|---|---|---|---|---|
| | | 1 | 2 | 3 | 4 | 5 | 6 | 7 | 3 | 4 |
| ω3 | C18:3 | 5 | 0 | 11 | 0 | 0 | 0 | 4 | 0 | 0 |
| | C20:5 | 4 | 12 | 12 | 7 | 7 | 7 | 3 | 15 | 15 |
| | C22:6 | 23 | 6 | 7 | 44 | 22 | 46 | 23 | 8 | 8 |
| Monoenoic | C16:1 | 2 | 4 | 8 | 3 | 4 | 3 | 2 | 9 | 9 |
| | C18:1 | 34 | 49 | 6 | 13 | 23 | 11 | 17 | 4 | 4 |
| | C20:1 | 2 | 0 | 4 | 1 | 3 | 1 | 1 | 5 | 5 |
| | C22:1 | 1 | 0 | 4 | 1 | 1 | 1 | 1 | 5 | 5 |
| ω6 | C18:2 | 11 | 7 | 4 | 2 | 4 | 2 | 27 | 2 | 2 |
| Saturated | C16:0 | 7 | 9 | 15 | 11 | 16 | 11 | 11 | 17 | 17 |
| | C18:0 | 2 | 2 | 4 | 3 | 4 | 3 | 3 | 4 | 4 |

Measured by gas chromatography after methylation.

TABLE 2

Principal fatty acid composition in triglyceride

| | | Example | | | | | | | Comp. Ex. | | | |
|---|---|---|---|---|---|---|---|---|---|---|---|---|
| | | 1 | 2 | 3 | 4 | 5 | 6 | 7 | 1 | 2 | 3 | 4 |
| ω3 | C18:3 | 5 | 0 | 63 | 10 | 6 | 7 | 4 | 10 | 0 | 0 | 0 |
| | C20:5 | 4 | 12 | 0 | 0 | 2 | 2 | 3 | 0 | 15 | 15 | 15 |
| | C22:6 | 23 | 6 | 0 | 0 | 6 | 14 | 23 | 0 | 8 | 8 | 8 |
| Mono- | C16:1 | 2 | 4 | 0 | 0 | 1 | 1 | 2 | 0 | 9 | 9 | 9 |
| enoic | C18:1 | 34 | 49 | 15 | 57 | 24 | 43 | 17 | 57 | 4 | 4 | 4 |
| | C20:1 | 2 | 0 | 0 | 2 | 1 | 2 | 1 | 2 | 5 | 5 | 5 |
| | C22:1 | 1 | 0 | 0 | 1 | 0 | 1 | 1 | 1 | 5 | 5 | 5 |
| ω6 | C18:2 | 11 | 7 | 14 | 21 | 40 | 15 | 27 | 21 | 2 | 2 | 2 |
| Saturated | C16:0 | 7 | 9 | 5 | 4 | 12 | 6 | 11 | 4 | 17 | 17 | 17 |
| | C18:0 | 2 | 2 | 4 | 2 | 4 | 2 | 3 | 2 | 4 | 4 | 4 |

Measured by gas chromatography after methylation.

TEST EXAMPLE 1

Investigation of Cell Membrane Fluidity-Improving Effect:

Wistar mail rats aged 10 weeks were divided into 7 groups, and a feed (see Table 3) containing corn oil (10%) and one (4%) of Oil Compositions 1 to 5 and 8 to 10 was given to its corresponding group for 2 weeks. The microsomes were then taken out of the liver of each rat to determine a total cholesterol quantity and a phospholipid quantity, thereby finding a ratio of the total cholesterol quantity to the phospholipid quantity. The results are shown in Table 4. In the table, the numerical values indicate relative values that a value in the case where a feed (control) containing only corn oil (10%) was used is regarded as 100. The smaller relative value indicates that the fluidity of a liver microsome cell membrane was more improved ("Nippon Shokuhin Kagaku Kogaku Kaishi", Vol. 43, page 1231, 1996).

TABLE 3

| | Control | Oil Composition 1–5, 8–10 |
|---|---|---|
| Casein | 20 | 20 |
| Corn oil | 10 | 10 |
| Oil composition | 0 | 4 |
| Mineral mixture | 4 | 4 |
| Vitamin mixture | 1 | 1 |
| Cellulose | 4 | 4 |
| Choline chloride | 0.15 | 0.15 |
| Starch | 60.85 | 56.85 |

TABLE 4

| Oil composition | Total cholesterol/phospholipid* |
|---|---|
| 1 | 80 |
| 2 | 87 |
| 3 | 92 |
| 4 | 74 |
| 5 | 87 |
| 8 | 110 |
| 9 | 98 |
| 10 | 95 |
| Control | 100 |

*Indicated by relative values that a value in the case where the feed (control) containing only corn oil (10%) was used is regarded as 100.

Oil Compositions 1 to 5 according to the present invention exhibited a cell membrane fluidity-improving effect superior to Oil Compositions 8 to 10.

TEST EXAMPLE 2

Investigation of Improvement in Resistance to Oxidation:

Each (20 g) of deodorized Oil Compositions 1 to 5, 9 to 11 and 12 to 15 was placed in a 50-mL sample bottle, and the bottle was left at rest in an opened state for 5 days in a thermostat controlled at 40° C. Thereafter, an absorbance at 532 nm was measured in accordance with the thiobarbituric acid method ("Yukagaku", Vol. 24, page 481, 1975). The amount of malondialdehyde (MDA) was determined by using 1,1,3,3-tetraethoxypropane to prepare a calibration curve. The results are shown in Table 5.

TABLE 5

| Oil composition | Amount of MDA (mg/kg) |
|---|---|
| 1 | 8.7 |
| 2 | 4.5 |
| 3 | 7.2 |
| 4 | 8.9 |
| 5 | 6.4 |
| 9 | 13.2 |
| 10 | 14.1 |
| 11 | 18.5 |
| 12[1] | 2.0 |
| 13[2] | 4.6 |
| 14[3] | 3.7 |
| 15[4] | 4.1 |

[1]Oil Composition 12:
Oil Composition 2                98.0%
Sankatol No 1*                    2.0
(Taiyo Chemical)
[2]Oil Composition 13:
Oil Composition 4                99.9%
Teafuran 90S**                   0.04
(Itoen)
Vitamin C palmitate              0.04
(Roche)
Mix Vitamin E MDE-6000          0.02
(Yashiro)
*Catechin content                10%
**Catechin content               90%
[3]Oil Composition 14:
Obtained by replacing Oil Composition 2
in Oil Composition 12 by Oil Composition 6.
[4]Oil Composition 15:
Obtained by replacing Oil Composition 4
in Oil Composition 13 by Oil Composition 7.

Oil Compositions 1 to 5 and 12 to 15 according to the present invention were superior in oxidation stability to Oil Compositions 9 to 11.

TEST EXAMPLE 3

Each (20 g) of Oil Compositions 1 to 7, 9 and 10 was placed in a 50-mL sample bottle, and the bottle was tightly stoppered and left at rest at 5° C. for 3 hours and then at 35° C. for 0.5 hours. Thereafter, the appearance of the oil composition was visually observed to evaluate it in accordance with the following standard.

TABLE 6

| Oil composition | Evaluation |
|---|---|
| 1 | ⊚ |
| 2 | ⊚ |
| 3 | ⊚ |
| 4 | ⊚ |
| 5 | ⊚ |
| 6 | ⊚ |
| 7 | ⊚ |
| 9 | Δ |
| 10 | x |

⊚: No turbidity was observed;
o: Turbidity was scarcely observed;
Δ: Turbidity was slightly observed;
x: Turbidity was observed.

No turbidity was observed on all the oil compositions according to the present invention.

TEST EXAMPLE 4

Common salt (0.5 g) and pepper (0.1 g) were added to the whole egg (100 g), the egg was sufficiently beaten up, a sample oil composition (5 g) was placed on a frying pan (24 cm), and the frying pan was put over a fire (city gas flow rate: 2.2 L/min). After 30 seconds, the egg previously beaten was put into the frying pan and heated for 20 seconds while scrambling with chopsticks to cook scrambled egg. The scrambled egg was dished to organoleptically evaluate it by 10 panelists in accordance with the following standard.
Evaluation Standard:
5: Very delicious;
4: Delicious;
3: It is a toss-up whether the dish was delicious or not;
2: Not very delicious;
1: Not delicious.

The average values of evaluation scores are shown in Table 7.

TABLE 7

| Oil composition | Evaluation |
|---|---|
| 1 | 3.8 |
| 2 | 4.3 |
| 3 | 4.0 |
| 4 | 3.8 |
| 5 | 4.1 |
| 10 | 1.7 |

The flavor of the scrambled egg cooked with each of the oil compositions according to the present invention was evaluated as delicious.

TEST EXAMPLE 5
Evaluation of French Dressing as to Flavor:

A wine vinegar (50 parts by weight) was mixed with common salt (2.5 parts by weight), pepper (0.6 parts by weight) and mustard (0.5 parts by weight). Oil Composition 1 or 6 (90 parts by weight) was added to the resultant mixture while stirring by a whipper. The resultant mixture was sufficiently stirred to prepare a French dressing. The dressing was put on coleslaw to evaluate it as to flavor by ten panelists in accordance with the above-described evaluation standard. As a result, the average values were 4.1 and 4.0, respectively, and the French dressings were evaluated as delicious.

TEST EXAMPLE 6
Evaluation of Oral Syrup Preparation as to Flavor:

After sodium benzoate (0.06 parts by weight) and purified sucrose (50 parts by weight) were added to heated purified water (40 parts by weight) into a solution, hydroxypropyl cellulose (0.5 parts by weight) was added, and the mixture was stirred by a homomixer into a solution, thereby preparing Liquid A. On the other hand, sucrose fatty acid ester (0.2 parts by weight) was dispersed in Oil Composition 5 or 7 (5 parts by weight) to prepare Liquid B. Liquid B was added while stirring Liquid B by the homomixer, and purified water (4.24 parts by weight) was added thereto, thereby formulating an oral syrup preparation. The syrup preparations thus obtained were evaluated at to flavor in the same manner as in Test Example 4. The average values thereof were 4.4 and 4.5, respectively, and the syrup preparations were evaluated as being good in flavor.

As described above, the oil compositions according to the present invention are hard to be oxidized because the content of the ω3 type unsaturated acyl group-containing diglyceride is relatively low, is excellent in flavor and can effectively exhibit the physiological activities of ω3 type unsaturated fatty acids.

What is claimed is:

1. An oil composition comprising:

i) 10–40% by weight of a diglyceride; and ii) 40.1 to 89.8% by weight of a triglyceride, wherein said diglyceride is comprised of at least 55% by weight of constitutive acyl groups as unsaturated acyl groups, and wherein from 15 to 100% by weight of said acyl groups are ω3 type unsaturated acyl groups having at least 20 carbon atoms; and wherein said triglyceride is comprised of at least 70% by weight of constitutive acyl groups as unsaturated acyl groups, and wherein from 5 to 80% by weight of said acyl groups are a linoleyl group.

2. The oil composition according to claim 1, wherein 10 to 85% by weight of said constitutive acyl groups in said triglyceride are monoenoic acyl groups.

3. The oil composition according to claim 1 or 2, which comprises 0.1 to 10% by weight of a monoglyceride.

4. The oil composition according to claims 1 or 2, which comprises 0.1 to 10% by weight of a glyceride polymer.

5. The oil composition according to claims 1 or 2, which comprises 0.01 to 5% by weight of an antioxidant.

6. The oil composition according to claims 1 or 2, wherein said ω3 type unsaturated acyl group has 20 to 24 carbon atoms.

7. The oil composition according to claims 1 or 2, wherein 20–90% by weight of said acyl groups are ω3 type unsaturated acyl groups having at least 20 carbon atoms.

8. The oil composition according to claims 1 or 2, wherein the number of carbon atoms in remaining acyl groups constituting said diglyceride is from 8 to 24.

9. The oil composition according to claims 1 or 2, wherein said triglyceride comprises monenoic acyl groups in a proportion of 10 to 85%.

10. A food comprising the oil composition according to claims 1 or 2.

11. A medicine comprising the oil composition according to claims 1 or 2 as an active ingredient.

* * * * *